United States Patent [19]
Bryan et al.

[11] Patent Number: 5,246,849
[45] Date of Patent: Sep. 21, 1993

[54] THERMALLY STABLE SERINE PROTEASES

[75] Inventors: Philip N. Bryan, Silver Spring; Michael W. Pantoliano, Germantown, both of Md.

[73] Assignee: Enzon, Inc., Piscataway, N.J.

[21] Appl. No.: 671,546

[22] Filed: Mar. 19, 1991

Related U.S. Application Data

[62] Division of Ser. No. 180,757, Apr. 12, 1988, Pat. No. 5,013,657.

[51] Int. Cl.$^5$ .................... C12N 9/50; C12N 9/52; C12N 9/54; C12N 15/00
[52] U.S. Cl. ............................ 435/220; 435/172.3; 435/222; 435/219; 435/221; 252/174.12; 8/137
[58] Field of Search .............. 435/221, 222, 69.1, 435/172.3; 536/27, 25, 23.2; 252/174.12

[56] References Cited

U.S. PATENT DOCUMENTS

| | | | |
|---|---|---|---|
| 4,749,511 | 6/1988 | Lad et al. | 252/174.12 |
| 4,760,025 | 7/1988 | Estell et al. | 435/222 |
| 4,828,994 | 5/1989 | Fahuestock et al. | 435/172.3 |
| 4,914,031 | 4/1990 | Zukowski et al. | 435/222 |
| 4,980,288 | 12/1990 | Bryan et al. | 435/222 |
| 4,990,452 | 2/1991 | Bryan et al. | 435/222 |
| 5,013,657 | 5/1991 | Bryan et al. | 435/172.3 |
| 5,116,741 | 5/1992 | Bryan et al. | 435/87 |

FOREIGN PATENT DOCUMENTS 130756  1/1985  European Pat. Off. ............ 435/221

OTHER PUBLICATIONS

Smith, E. L. et al., "Subtilisin Carlsberg-V. The Complete Sequence Comparison with Subtilisin BPN': Evolutionary Relationships", J. of Biological Chemistry 243(9):2184–2191 (1968).

Estell, P. A., et al., 1985, The Journal of Biological Chemistry, 260 (11): 6518–6521.

Liao, H., et al., 1986, Proc. Natl. Acad. Sciences USA, 83:576–580.

Estell, P. A., et al., 1984, World Biotechnology Report, 2: 181–187.

Pantoliano, M. W., et al., 1987, Biochemistry, 26: 2077–2082.

Bryan, P. N., et al., 1986, Proteins: Structure, Function and Genetics, 1:326–334.

Cunningham, B. C., et al., 1987, Protein Engineering 1 (4): 319–325.

Bryan, P., et al., 1986, Proc. Nat'l. Acad. Sciences USA 83: 3743–3745.

Vasanthar, N., et al., 1983, Genetics and Biotechnology of Bacilli, 2: 163–172.

Wells, J. A., et al., 1983, Genetics and Biotechnology of Bacilli, 2: 173–180.

Shortle, P., et al., 1978, Proc. Nat'l. Acad. Sciences USA, 75:2170–2174.

Vasantha, N., et al., 1984 Journal of Bacteriology, 158(2):811–819.

Jacobs, M., et al., 1985, Nucleic Acids Research, 13(24):8913–8926.

Nedkov, P., et al., 1985, Biol. Chem. Hoppe-Seyler, 366: 421–430.

Kurihara, M., et al., 1972, The Journal of Biologicol Chemistry 274 (17): 5619–5631.

Svendsen, I., et al., 1986, FEBS Letters, 196(2): 228–232.

Meloun, B., et al., 1985 FEBS Letters, 183(2): 195–200.

Jany, K.-D., et al., 1985, Biol. Chem. Hoppe-Seyler, 366: 485–492.

Pähler, A., et al., 1984, The EMBO Journal, 3(6): 1311–1314.

McPhalen, C. A., et al., 1985, FEBS Letters, 188(1): 55–58.

(List continued on next page.)

Primary Examiner—Robert A. Wax
Assistant Examiner—William W. Moore
Attorney, Agent, or Firm—Sterne, Kessler, Goldstein & Fox

[57] ABSTRACT

The invention relates to subtilisin enzymes which have been modified by mutating a nucleotide sequence (gene) coding for the subtilisin. The modified subtilisin enzymes have enhanced thermal stability.

5 Claims, No Drawings

OTHER PUBLICATIONS

Myers, R. M., et al., 1985, Science, 229: 242–247.
Folk, W. R., et al., 1983 Cell 33: 585–593.
Wells, J. A., et al., 1983, Nucleic Acids Research 11(22): 7911–7925.
Wells, J. A., et al., 1987, Proc. Nat'l. Acad. Sciences USA 84: 5167–5171.
Carter, P., et al., 1988, Nature 332: 564–568.
Owers Narhi, L., et al., 1988, Archives of Biochemistry and Biophysics, 261 (1): 161–169.
Rollence, M. L., et al., 1988, CRC Critical Reviews in Biotechnology 8(3): 217–224.
Estell, D. A., et al., 1987, Journal of Cellular Biochemistry UCLA Symposia Abstract No. 24, Supplement 11C, p. 200.
Bryan, P., et al., 1986, Federation Proceedings 45(6): 1519, Abstract 226, Meeting, American Society of Biologicol Chemists.
Thomas, P. G., et al., 1986 Nature 318: 375–376.
Estell, D. A., et al., 1986 Science 233: 659–663.
Carter, P., et al., 1987 Science 237: 394–399.
Sternberg, M. J. E., et al., 1987, Nature 330: 86–88.
Russell, A. J., et al., 1987, The Journal of Molecular Biology 193: 803–813.
Wells, J. A., et al., 1987, Proc. Nat'l. Acad. Sciences, USA 84: 1219–1223.
Bryan, P. N., et al., 1985, Journal of Cellular Biochemistry, UCLA Symposia Abstract 0632, Supplement 9B, p. 92.
Mitchienon, L., et al., 1987, Journal of Cellular Biochemistry UCLA Symposia Abstract N516, Supplement 11C, p. 245.
Stahl, M. L., et al., 1984, Journal of Bacteriology, 158 (2): 411–418.
Zoller, M. S., et al., 1983, Methods in Enzymology 100: 468–500.
Band, L., et al., 1987, Journal of Bacteriology, 169 (1): 444–446.

THERMALLY STABLE SERINE PROTEASES

This application is a division of application Ser. No. 07/180,757, filed Apr. 12, 1988, now U.S. Pat. No. 5,513,657, filed May 7, 1991.

FIELD OF THE INVENTION

The invention pertains to modified subtilisin enzymes which have enhanced thermal stability and to the genes which encode the subtilisin enzymes.

BACKGROUND OF THE INVENTION

Proteins are linear polymers of amino acids. Since the polymerization reactions which produce proteins result in the loss of one molecule of water from each amino acid, proteins are often said to be composed of amino acid "residues." Natural protein molecules may contain as many as 20 different types of amino acid residues, each of which contains a distinctive side chain. The sequence of amino acids in a protein defines the primary structure of the protein.

Proteins fold into a three-dimensional structure. The folding is determined by the sequence of amino acids and by the protein's environment. The remarkable properties of proteins depend directly from the protein's three-dimensional conformation. Thus, this conformation determines the activity or stability of enzymes, the capacity and specificity of binding proteins, and the structural attributes of receptor molecules.

The three-dimensional structure of a protein may be determined in a number of ways. Perhaps the best known way of determining protein structure involves the use of the technique of X-ray crystallography. An excellent general review of this technique can be found in *Physical Biochemistry*, Van Holde, K. E. (Prentice-Hall, N.J. (1971) pp221-239) which reference is herein incorporated by reference. Using this technique, it is possible to elucidate three-dimensional structure with remarkable precision. It is also possible to probe the three-dimensional structure of a protein using circular dichroism, light scattering, or by measuring the absorption and emission of radiant energy (Van Holde, *Physical Biochemistry*, Prentice-Hall, N.J. (1971)). Additionally, protein structure may be determined through the use of the techniques of neutron defraction, or by nuclear magnetic resonance (*Physical Chemistry*, 4th Ed. Moore, W. J., Prentice-Hall, N.J. (1972) which reference is hereby incorporated by reference).

The examination of the three-dimensional structure of numerous natural proteins has revealed a number of recurring patterns. Alpha helices, parallel beta sheets, and anti-parallel beta sheets are the most common patterns observed. An excellent description of such protein patterns is provided by Dickerson, R. E., et al. In: *The Structure and Action of Proteins*, W. A. Benjamin, Inc., CA (1969). The assignment of each amino acid to one of these patterns defines the secondary structure of the protein. The helices, sheets and turns of a protein's secondary structure pack together to produce the three-dimensional structure of the protein. The three-dimensional structure of many proteins may be characterized as having internal surfaces (directed away from the aqueous environment in which the protein is normally found) and external surfaces (which are in close proximity to the aqueous environment). Through the study of many natural proteins, researchers have discovered that hydrophobic residues (such as tryptophan, phenylalanine, tyrosine, leucine, isoleucine, valine, or methionine) are most frequently found on the internal surface of protein molecules. In contrast, hydrophilic residues (such as aspartic acid, asparagine, glutamate, glutamine, lysine, arginine, histidine, serine, threonine, glycine, and proline) are most frequently found on the external protein surface. The amino acids alanine, glycine, serine and threonine are encountered with equal frequency on both the internal and external protein surfaces.

Proteins exist in a dynamic equilibrium between a folded, ordered state and an unfolded, disordered state. This equilibrium in part reflects the short range interactions between the different segments of the polypeptide chain which tend to stabilize the protein's structure, and, on the other hand, those thermodynamic forces which tend to promote the randomization of the molecule.

The largest class of naturally occurring proteins is made up of enzymes. Each enzyme generally catalyzes a different kind of chemical reaction, and is usually highly specific in its function. Enzymes have been studied to determine correlations between the three-dimensional structure of the enzyme and its activity or stability.

The amino acid sequence of an enzyme determines the characteristics of the enzyme, and the enzyme s amino acid sequence is specified by the nucleotide sequence of a gene coding for the enzyme. A change of the amino acid sequence of an enzyme may alter the enzyme's properties to varying degrees, or may even inactivate the enzyme, depending on the location, nature and/or magnitude of the change in the amino acid sequence.

Although there may be slight variations in a distinct type of naturally occurring enzyme within a given species of organism, enzymes of a specific type produced by organisms of the same species generally are substantially identical with respect to substrate specificity, thermal stability, activity levels under various conditions (e.g., temperature and pH), oxidation stability, and the like. Such characteristics of a naturally occurring or "wild-type" enzyme are not necessarily optimized for utilization outside of the natural environment of the enzyme. It may thus be desirable to alter a natural characteristic of an enzyme to optimize a certain property of the enzyme for a specific use, or for use in a specific environment.

SUMMARY OF THE INVENTION

The invention relates to modified subtilisin enzymes which have increased thermal stability. In addition, the invention pertains to cloned mutant genes coding for a subtilisin material having at least one amino acid substitution which has increased thermal stability over wild-type subtilisin.

Definitions

The following definitions are used in describing the invention.

Protein

A protein is a heteropolymer made by living cells and composed of amino acids. A typical protein comprises 100 to 1000 amino acids. The exact sequence of amino acids determines the structure and function of the protein.

Amino acid

Amino acids are naturally occurring compounds that are the building blocks of proteins. The natural amino acid are usually abbreviated to either three letters or one letter. The most common amino acids, and their symbols, are given in Table 1. The amino acids are joined head to tail to form a long main chain. Each kind of amino acid has a different side group.

TABLE 1

| Amino acid names and abbreviations. | | |
|---|---|---|
| Amino Acid | Three letter code | Single letter code |
| Alanine | Ala | A |
| Arginine | Arg | R |
| Aspartic acid | Asp | D |
| Asparagine | Asn | N |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophane | Trp | W |
| Tyrosine | Tyr | Y |
| Valine | Val | V |

Atom names

All amino acids have the same atoms in the main chain and differ only in the side chains. The main-chain atoms are a nitrogen, two carbons, and one oxygen. The first atom is the nitrogen, called N. The next atom is a carbon and is called the alpha-carbon. Side groups are attached to this alpha-carbon. The alpha-carbon is connected to the carbonyl carbon which is called C. C is connected tot he carbonyl oxygen (called O ) and to the N of the next residue. The side group atoms are given names composed of the symbol for the element (C, O, N, S), a Greek letter (alpha, beta, gamma, delta, epsilon, zeta and eta), and perhaps an arabic numeral if the side group is forked.

DETAILED DESCRIPTION OF THE INVENTION

This invention pertains to subtilisin enzymes that have been modified by mutating the various nucleotide sequences that code for the enzymes. The modified subtilisn enzymes of this invention have enhanced thermal stability.

The subtilisin enzymes of this invention belong to a class of enzymes known as proteases. A protease is a catalyst for the cleavage of peptide bonds. An example of this cleavage is given below.

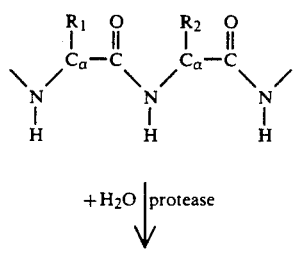

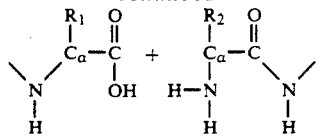

One type of protease is a serine protease. A serine protease will catalyze the hydrolysis of peptide bonds in which there is an essential serine residue at the active site. Serine proteases can be inhibited by phenylmethanesulfonylfluoride and by diisopropylfluorophosphate.

A subtilisin is a serine protease produced by Gram positive hacteria or by fungi. The amino acid sequences of seven subtilisins are known. These include five subtilisins from Bacillus strains (subtilisin BPN', subtilisin Carlsberg, subtilisin DY, subtilisin amylosacchariticus, and mesenticopeptidase). (Vasantha et al., "Gene for alkaline protease and neutral protease from *Bacillus amyloliouefaciens* contain a large open-reading frame between the regions coding for signal sequence and mature protein," *J. Bacteriol.* 159:811-819 (1984); Jacobs et al., "Cloning sequencing and expression of subtilisin Carlsberg from *Bacillus licheniformis,*" *Nucleic Acids Res.* 13:8913-8926 (1985); Nedkov et al., "Determination of the complete amino acid sequence of subtilisin DY and its comparison with the primary structures of the subtilisin BPN', Carlsberg and amylosacchariticus,"*Biol. Chem. Hoppe-Seyler* 366:421-430 (1985); Kurihara et al., "Subtilisin amylosacchariticus," *J. Biol. Chem.* 247:5619-5631 (1972); and Svendsen et al., "Complete amino acid sequence of alkaline mesentericopeptidase," *FEBS Lett.* 196:228-232 (1986)).

The amino acid sequence of the subtilisin thermitase from *Thermoactinomvces vuloaris* is also known. (Meloun et al., "Complete primary structure of thermitase from *thermoactinomvces vuloaris* and its structural features related to the subtilisin-type proteases," *FEBS Lett.* 183:195-200 (1985).)

The amino acid sequences from two fungal proteases are known: proteinase K from *Tritirachium album* (Jany et al., "Proteinase K from Tritirachium albam Limber," *Biol. Chem. Hoppe-Sevler* 366:485-492 (1985)) and thermomycolase from the thermophilic fungus, *Malbranchea pulchella* (Gaucher et al., "Endopeptidases: Thermomycolin," *Methods Enzymol.* 45:415-433 (1976)).

These enzymes have been shown to be related to subtilisin BPN', not only through their primary sequences and enzymological properties, but also by comparison of x-ray crystallographic data. (McPhalen et al., "Crystal and molecular structure of the inhibitor eglin from leeches in complex with subtilisin Carlsberg," *FEBS Lett.* 188:55-58 (1985) and Pahler et al., "Three-dimensional structure of fungal proteinase K reveals similarity to bacterial subtilisin," *EMBO J.* 3:1311-1314 (1984).)

As used in this invention, the term "mutated or modified subtilisin enzyme(s)" is meant to include mutated serine proteases that have enhanced thermal stability, and are homologous to the subtilisin enzymes of this invention. The mutated or modified subtilisin enzymes are also described herein as "subtilisin material." As used herein, and under the definition of mutated or modified subtilisin enzyme or subtilisin material, the mutations of this invention may be introduced into any serine protease which has at least 50%, and preferably 80% amino acid sequence homology with the sequences for subtilisin BPN', subtilisin Carlsberg, subtilisin DY, subtilisin amylosacchariticus, mesenticopeptidase, thermitase, proteinase K, or thermomycolase and therefore may be considered homologous.

The mutated subtilisin enzymes of this invention have enhanced thermal stability over native or wild-type subtilisin. Thermal stability is a good indicator of the overall robustness of a protein. Proteins of high thermal stability often are stable in the presence of chaotropic agents, detergents, and under other conditions, which tend to inactivate proteins. Thermally stable proteins are therefore expected to be useful for many industrial and therapeutic applications, in which resistance to high temperature, harsh solvent conditions or extended shelf-life is required.

specific amino acid substitution that enhances thermal stability. Table 2 shows the strain designation of the host cell secreting the subtilisin. The mutation is the amino acid substitution with the naturally occuring amino acid and position number given first with the arrow to the right indicating the amino acid substitution. The ratio of mutant T½ to wild-type T½ is given next. Finally, the oligonucleotide is given: The first line in this last column is the number (#) designation which indicates a specific oligonucleotide. The second line, below the oligonucleotide number, is the nucleotide or base pair sequence of the oligonucleotide. The mutations were made using subtilisin BPN'. However, as explained herein these mutations can be introduced at analogous positions in serine proteases using oligonucleotide-directed mutagenesis.

TABLE 2

Mutated Subtilisin BPN' Enzymes.

| Strain | Mutation | T½ compared to wild type enzyme | | Mutagenic Oligonucleotide |
|---|---|---|---|---|
| | | 10 mM CaCl | 1.0 mM EDTA | |
| GX7130 | Wild Type | 1.0 | 1.0 | — |
| GX7174 | VAL8 → ILE | 2.0 | 0.8 | #2010 21-mer<br>CCT TAC GGC ATC TCA CAA ATT |
| GX7175 | GLY169 → ALA | 5.9 | 1.1 | #2011 21-mer<br>GGC TAC CCT GCG AAA TAC CCT |
| GX7195 | TYR217 → LYS | 3.3 | 2.7 | #1928 19-mer<br>CGG GGC GAA AAA CGG TAC G |
| GX8303 | MET50 → PHE | 0.76 | 1.4 | #2207 19-mer<br>GAG CCA GCT TCG TTC CTT C |
| GX8309 | SER248 → ASP | 1.5 | 0.75 | #2208 24-mer<br>CAA GTC CGC GAC AGA TTA GAA AAC |
| | SER249 → ARG | | | #2208 24-mer |
| GX8314 | GLN206 → CYS | 2.4 | 5.1 | #2181 19-mer<br>GTA TCT ATC TGT AGC ACG C |
| GX8330 | TYR217 → LEU | 2.0 | 1.8 | #2331 19-mer<br>CGG GGC GCT TAA CGG TAC G |
| GX8336 | GLN206 → TYR | 1.1 | 1.7 | #2422 19-mer<br>GTA TCT ATC TAC AGC ACG C |
| GX8352 | SER63 → ASP | 6.3 | — | #2494 21-mer<br>GAC AAC AAC GAC CAC GGA ACT |
| | TYR217 → LYS | | | #1928 19-mer |
| GX8354 | GLN271 → GLU | 1.3 | — | #2522 17-mer<br>CAA CGT AGA AGC GGC AG |
| GX8363 | THR22 → LYS | 1.3 | 2.1 | #2524 18-mer<br>AGG CTA CAA AGG ATC AAA |
| | ASN76 → ASP | | | #2463 20-mer<br>CGG CTC TTG ACA ACT CAA TC |
| GX8376 | TYR104 → VAL | 5.0 | 1.6 | #2332 19-mer<br>CGG CCA AGT TAG CTG GAT C |
| | GLY128 → SER | | | #2338 19-mer<br>GCC TCG GCT CTC CTT CTG G |

As used herein, resistance to thermal inactivation is measured by resistance to thermal inactivation under two representative sets of conditions. The first is in the presence of 10 mM calcium chloride at 65° C. and the second is at 45° C. in the presence of 10 mM EDTA, which removes free calcium from solution. Calcium is known to stabilize subtilisin. Measurements of stability under these two extremes of calcium concentration were made because potential commercial uses of stable subtilisins could involve conditions with varying amounts of calcium present. The T½ of wild type BPN' subtilisin is 59±3 minutes in 10 mM CaCl at 65° C. and 14.4±0.05 minutes in 1 mM EDTA at 45° C. The thermal stability of the mutated subtilisin is expressed as a ratio of T½ (mutant) divided by the T½ (wild-type).

The mutated subtilisin enzymes detailed in Table 2 have been found to be thermally stable. The mutated subtilisin enzymes of this invention have at least one Using the information of the subtilisn enzyme mutations of Table 2, one can improve other proteases which are closely related, subtilisin Carlsberg for example. Closeness of relation is measured by comparison of amino acid sequences. There are many methods of aligning protein sequences, but the differences are only manifest when the degree of relatedness is quite small. The methods described in *Atlas of Protein Sequence and Structure*, Margaret O. Dayhoff editor, Vol. 5 Supplement 2, 1976, National Biomedical Research Foundation, Georgetown University Medical Center, Washington, D.C., p. 3 ff., entitled SEARCH and ALIGN, define relatedness. As is well known in the art, related proteins can differ in number of amino acids as well as identity of each amino acid along the chain. That is, there can be deletions or insertions when two structures are aligned for maximum identity. For example, subtilisin Carlsberg has only 274 amino acids, while subtilisin BPN' has 275 amino acids. Aligning the two sequences shows that Carlsberg has no residue corresponding to ASN56 of subtilisin BPN'. Thus the amino acid sequence of Carlsberg would appear, for example, very different from BPN' unless a gap is recorded at location 56. Therefore, one can predict with high degree of confidence that, substituting TYR for LYS at location 217 of subtilisin Carlsberg will increase thermal stability, provided that the residues in Carlsberg are numbered by homology to BPN'.

When one of the two homologous subtilisins has a gap, one must infer that the structures are different at that position. Examples of such differences are well known in the art. Because of these local differences, one should not transfer stabilizing mutations if either subtilisin has a gap at, or immediately adjacent, to the site of the mutation. Therefore, after aligning the amino acid sequences, those mutations at or next to gaps are deleted from the list of desirable mutations and the mutation is not made.

One can use this reasoning to transfer all of the thermostable mutations described herein to other homologous serine proteases.

In brief, in order to introduce the enhanced themostable mutation(s) of this invention, the gene coding for the desired subtilisin material generally is first isolated from its natural source and cloned in a cloning vector. Alternatively, mRNA which is transcribed from the gene of interest can be isolated from the source cell and converted into cDNA by reverse transcription for insertion into a cloning vector. A cloning vector can be a phage or plasmid, and generally includes a replicon for autonomous replication of the vector in a microorganism independent of the genome of the microorganism. A cloning vector advantageously includes one or more phenotypic markers, such as DNA coding for antibiotic resistance, to aid in selection of microorganisms transformed by the vector.

Procedures for insertion of DNA or cDNA into a vector for cloning purposes are well known in the art. These procedures generally include insertion of the gene coding for the subtilisin material into an opened restriction endonuclease site in the vector, and may involve addition of homopolymeric tails of deoxynucleotides to the ends of the gene and linking the gene to opened ends of a cloning vector having complementary homopolymeric tails. A subtilisin gene can then be mutated by oligonucleotide-directed mutagenesis. Oligonucleotide-directed mutagenesis, also called site-directed mutagenesis, is described in detail in Bryan et al., *Proc. Natl. Acad. Sci. USA* 83:3743-3745 (1986), incorporated herein by reference.

The mutant subtilisin material of this invention can be used as an additive to washing preparations, such as detergents, which are used for cleaning, in particular for cleaning clothes. The mutant subtilisin material of this invention is more thermally stable than wild-type subtilisin material and thus does not lose activity as rapidly as wild-type when stored in solution with detergents or when subjected to high heat during use in cleaning. By use of the mutant subtilisin material of this invention as an additive in washing preparations, the removal of proteinaceous stains on fabric is improved. The amount of mutant subtilisin material that may be used as an additive to washing preparations are well known in the art, or may readily be ascertained by routine experimentation. The optimal range of enzyme concentration will, of course, be related to the cost of the enzyme and the amount of cleaning needed. Typically, the amount of mutated subtilisin material added to a washing preparation will be from about 2000 to about 4000 Alkaline Delft Units/gram (ADU/gm) of washing preparation.

The invention is illustrated by the following examples which are not intended to be limiting.

EXAMPLES

Example I

Thermostability Studies

The subtilisin gene from *Bacillus amyloliouefaciens* (subtilisin BPN') has been cloned and sequenced previously and expressed at high levels from its natural promoter sequences in *Bacillus subtilis* (Vasantha et al., *Bacteriol.* 159:881 (1984); Wells et al., *Nucleic Acids Res.* 11.7911 (1983)). Mutations were introduced in vitro into the plasmid-encoded subtilisin gene and their effect on the thermostability of the altered enzyme was analyzed.

All mutant genes were recloned into a pUB110 based expressed plasmid and used to transform *B. subtilis*. The *B. subtilis* strain used as the host contains a chromosomal deletion of its subtilisin gene and therefore produces no background wild type activity. All mutant enzymes were efficiently expressed from this vector and were secreted into the culture medium at a concentration of about 1 g/l. Subtilisin is the major secreted protein in this system and comprises almost 80% of the total extracellular protein.

Purification

The mutated subtilisin enzymes were purified from cell-free fermentation broths by means of the following three-step purification scheme:

(1) DEAE chromatography of crude fermentation broth. The broth was adjusted to pH 7.0 by addition of solid 2-(N-morpholino)-ethanesulfonic acid (Mes) and loaded onto a bed (13×5 cm) of DE-52 cellulose (Whatman) which was previously equilibrated with 20 mM Mes buffer (pH 7.0). Subtilisin washes through unretarded under these conditions.

(2) Acetone fractionation of DEAE eluate. Acetone (−20° C.) was stirred with the DEAE eluate at 4° C. Subtilisin precipitates between 50 and 70% acetone. The fraction the precipitates between 0 and 50% acetone was discarded.

(3) SE-53 (Whatman) chromatography of acetone precipitate. The acetone precipitated subtilisin was dissolved in 20 mM Mes buffer (pH 6.0) and loaded onto a column (2.5×16 cm) of SE-53 cellulose equilibrated with the same buffer. A linear salt gradient (0 to 0.2M NaCl) was used to elute the subtilisin.

Fractions containing the highest specific activities were pooled and stored at −20° C. either as 70% isopropanol or 50% ammonium sulfate precipitants.

Enzyme Assay

Subtilisin activity was assayed by monitoring the hydrolysis of 1.0 mM solutions of the substrate, succinyl(L)-Ala-(L)-Ala-(L)-Pro-(L)-Phe-p-nitroanilide (SAAPF-pNA (Calbiochem)), in 50 mM Tris HCl (pH 8.0), 50 mM KCl at 25° C. One unit of activity corresponds to the amount of enzyme that hydrolyzes 1 umole of substrate per min. under these conditions. One of the products of hydrolysis, p-nitroanilide, has an extinction coefficient of 8800 $M^{-1}cm^{-1}$ at 410 nm, thus allowing easy monitoring of the enzymatic reaction (Delmar et al., *Anal. Biochem.* 99:316–320 (1979)). Subtilisin concentrations were estimated by 280 nm using $E_\alpha(.1\%)=1.17$ (Ottesen & Svendson, *Methods in Enzymology* (1976), p. 207).

Resistance to Thermal Inactivation

The mutated subtilisin enzymes were tested for resistance to thermal inactivation in solution. Thermal inactivation studies were performed by incubating a subtilisin solution dissolved in 10 mM $CaCl_2$, 50 mM Tris-HCl pH 8.0 or 1.0 mM EDTA, 50 mM Tris-HCl, pH 8.0. The presence of $CaCl_2$ stabilizes subtilisin. The sample was placed in a glass Durham tube which was immersed in a thermostated circulated water bath equilibrated at 65° C. in the presence of 10 mM $CaCl_2$ or 45° C. in the presence of 1 mM EDTA. Evaporation from the sample tube was prevented by sealing with Parafilm. Aliquots were removed at various time points and assayed by the assay solution at 25° C. The time zero measurement was the rate of hydrolysis of SAAPF-pNA before the sample is immersed in the temperature bath. All subsequent rates of hydrolysis of substrate were measured after immersion in the bath. Plots of the logarithm of the remaining activity versus time were found, for the most part, to be linear over the course of three half-lives. Thus, a first order rate law is applicable. The rate of loss of activity for subtilisin and the wild-type enzyme from strain 7130 at 65° C. in the presence of 10 mM $CaCl_2$, 50 mM KCl, and 50 mM Tris-HCl, pH 8.0, was found to have a half-life of $59\pm3$ minutes which agrees well with that reported in the literature for similar conditions (Voordouw et al., *Biochemistry* 15:3716–3724 (1976)). This rate was assigned the reference point 1.0 for wild-type enzyme. The half-life of thermal inactivation $(T\frac{1}{2})$ was measured for the mutated subtilisin enzymes. This information was presented in Table 2, above.

Although the foregoing invention has been described by way of illustration and example for purposes of clarity and understanding, it will be obvious that certain changes and modifications may be practiced within the scope of the invention, as limited only the scope of the appended claims.

What is claimed is:

1. A thermally stable substantially pure mutant subtilisin enzyme obtained by the following steps:
    (a) obtaining the amino acid sequence of a subtilisin;
    (b) aligning the amino acid sequence of said subtilisin with the amino acid sequence of subtilisin BPN';
    (c) mutating said subtilisin by oligonucleotide-directed mutagenesis to substitute cysteine at amino acid position 206, providing such mutation does not fall at or next to gaps in the amino acid sequence of said subtilisin of (a) and
    (d) producing a thermally stable mutant subtilisin enzyme.

2. A substantially pure mutant subtilisin enzyme comprising cysteine substituted for the amino acid at position 206 of the wild-type enzyme, wherein said subtilisin is a thermally stable mutated serine protease having at least 50% amino acid sequence homology with a subtilisin selected from the group consisting of BPN', Carlsberg, DY, amylosacchariticus, mesenticopepdidase, thermitase, proteinase K, and thermomycolase.

3. The subtilisin enzyme of claim 2, wherein said enzyme is mutated from a serine protease selected from the group of wild-type subtilisins consisting of subtilisin BPN', subtilisin Carlsberg, subtilisin DY, subtilisin amylosacchariticus, and mesentericopeptidase.

4. A washing preparation comprising the subtilisin enzyme of claim 2 at a concentration of 2,000 to 4,000 Alkaline Delft Units.

5. A method for improving the removal of proteinaceous stains on fabric comprising contacting said fabric with a washing preparation of claim 4 and cleaning said stained fabric with said washing preparation.

* * * * *

UNITED STATES PATENT AND TRADEMARK OFFICE
CERTIFICATE OF CORRECTION

PATENT NO. : 5,246,849

DATED : September 21, 1993

INVENTOR(S) : Bryan, et al

It is certified that error appears in the above-indentified patent and that said Letters Patent is hereby corrected as shown below:

On title page, Item [56]: under "OTHER PUBLICATIONS," left-hand column, change "Estell, P. A., et al." to --Estell, D. A., et al.-- (both occurrences); and
    page 2, right-hand column, change "Mitchienon, L., et al." to --Mitchinson, L., et al.--.

Column 1, line 6, change "5,513,657" to --5,013,657--.
Column 2, line 27, change "enzyme s" to --enzyme's--.
Column 3, line 5, change "acid" to --acids--; and
    line 41, change "tot he" to --to the--.
Column 4, line 16, change "hacteria" to --bacteria--;
    line 20, change "mesenticopeptidase" to --mesentericopeptidase--;
    line 22, change "amyloliouefaciens" to --amyloliquefaciens--;
    line 37, change "*Thermoactinomvces vuloaris*" to --*Thermoactinomyces vulgaris*--;
    line 39, change "*thermoactinomvces vuloaris*" to --*thermoactinomyces vulgaris*--;
    line 44, change "albam" to --album--.
Column 5, line 3, change "mesenticopeptidase" to --mesentericopeptidase--; and
    line 55, change "10 mM EDTA" to --1.0 mM EDTA--.

UNITED STATES PATENT AND TRADEMARK OFFICE
CERTIFICATE OF CORRECTION

PATENT NO. : 5,246,849  
DATED : September 21, 1993  
INVENTOR(S) : Bryan, et al It is certified that error appears in the above-indentified patent and that said Letters Patent is hereby corrected as shown below:

Column 8, line 13, change "*amylolioeufaciens*" to --*amyloliquefaciens*--;
   line 18, change "11.7911" to --11:7911--; and
   line 65, change "umole" to --μmole--.
Column 10, line 3, after "only" insert --by--; and
   line 24, change "mesenticopepdidase" to --mesentericopeptidase--.

Signed and Sealed this

Fourteenth Day of June, 1994

Attest:

BRUCE LEHMAN

*Attesting Officer*   Commissioner of Patents and Trademarks